US00PP16083P2

(12) United States Plant Patent
Niederländer

(10) Patent No.: US PP16,083 P2
(45) Date of Patent: Nov. 1, 2005

(54) ***ASTER* PLANT NAMED 'KIESTRBL'**

(50) Latin Name: *Aster dumosa*
Varietal Denomination: Kiestrbl

(75) Inventor: Andreas Niederländer, Bretzenheim (DE)

(73) Assignee: Kientzler GmbH & Co. KG, Gensingen (DE)

( * ) Notice: Subject to any disclaimer, the term of this patent is extended or adjusted under 35 U.S.C. 154(b) by 53 days.

(21) Appl. No.: 10/949,949

(22) Filed: Sep. 24, 2004

(51) Int. Cl.[7] ..... A01H 5/00
(52) U.S. Cl. ..... Plt./355
(58) Field of Search ..... Plt./355

*Primary Examiner*—Kent Bell
(74) *Attorney, Agent, or Firm*—C. A. Whealy

(57) ABSTRACT

A new and distinct cultivar of *Aster* plant named 'Kiestrbl', characterized by its uniform and mounded plant habit; freely branching growth habit; dark green-colored foliage; uniform flowering habit; daisy-type inflorescences with non-fading violet blue-colored ray florets and yellow-colored disc florets; flat and straight ray florets; and good container and garden performance.

1 Drawing Sheet

Botanical classification/cultivar designation: *Aster dumosa* cultivar Kiestrbl.

BACKGROUND OF THE INVENTION

The present Invention relates to a new and distinct cultivar of *Aster* plant, botanically known as *Aster dumosa* and hereinafter referred to by the name 'Kiestrbl'.

The new *Aster* is a product of a planned breeding program conducted by the Inventor in Bretzenheim, Germany. The objective of the program is to create or discover new potted *Aster* cultivars that have a uniform plant growth habit and freely flowering habit.

The new *Aster* originated from a cross-pollination made by the Inventor in 1997, in Bretzenheim, Germany, of a proprietary selection of *Aster dumosa* identified as code number 98-s-1495, not patented, as the female, or seed, parent with a proprietary selection of *Aster dumosa* identified as code number 98-r-1494, not patented, as the male, or pollen, parent. The new *Aster* was discovered and selected by the Inventor in 1998, as a single flowering plant from within the resulting progeny of the stated cross-pollination grown in a controlled environment in Bretzenheim, Germany. The selection of the new *Aster* was based on its uniform plant growth habit and freely flowering habit, and attractive ray floret coloration.

Asexual reproduction of the new *Aster* by terminal vegetative cuttings was first conducted in Bretzenheim, Germany. Asexual reproduction by cuttings and by tissue culture has shown that the unique features of this new *Aster* are stable and reproduced true to type in successive generations.

SUMMARY OF THE INVENTION

The cultivar Kiestrbl has not been observed under all possible environmental conditions. The phenotype may vary somewhat with variations in environment such as temperature and light level, without, however, any variance in genotype.

The following traits have been repeatedly observed and are determined to be the unique characteristics of 'Kiestrbl'.

These characteristics in combination distinguish 'Kiestrbl' as a new and distinct *Aster:*

1. Uniform and mounded plant habit.
2. Freely branching growth habit.
3. Dark green-colored foliage.
4. Uniform flowering habit.
5. Daisy-type inflorescences with non-fading violet blue-colored ray florets and yellow-colored disc florets.
6. Flat and straight ray florets.
7. Good container and garden performance.

Plants of the new *Aster* can be compared to plants of the female parent selection. In side-by-side comparisons conducted in Bretzenheim, Germany, plants of the new *Aster* differed from plants of the female parent selection in the following characteristics:

1. Plants of the new *Aster* were more uniform and more mounded in plant habit than plants of the female parent selection.
2. Plants of the new *Aster* were more vigorous than plants of the female parent selection.

Plants of the new *Aster* can be compared to plants of the male parent selection. In side-by-side comparisons conducted in Bretzenheim, Germany, plants of the new *Aster* differed from plants of the male parent selection in the following characteristics:

1. Plants of the new *Aster* were more freely flowering than plants of the male parent selection.
2. Ray florets of plants of the new *Aster* were more intense in color than ray florets of plants of the male parent selection.

Plants of the new *Aster* can be compared to plants of the cultivar Mittlemeer, not patented. In side-by-side comparisons conducted in Bretzenheim, Germany, plants of the new *Aster* differed from plants of the cultivar Mittlemeer in the following characteristics:

1. Plants of the new *Aster* were more freely flowering than plants of the cultivar Mittlemeer.
2. Plants of the new *Aster* had more ray florets than plants of the cultivar Mittlemeer.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster*.

The photograph on the top of the sheet comprises a close-up view of typical inflorescences of 'Kiestrbl'.

The photograph on the bottom of the sheet comprises a side perspective view of a typical flowering plant of 'Kiestrbl' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered in 12.7-cm containers during the spring in Bonsall, Calif., in an outdoor nursery and under conditions which approximate those generally used in commercial potted *Aster* production. During the production of these plants, day temperatures ranged from 13 to 24° C. and night temperatures ranged from 2 to 7° C. Plants were about three months old when the photographs and description were taken.

Botanical classification: *Aster dumosa* cultivar Kiestrbl.

Parentage:

*Female, or seed, parent.*—Proprietary selection of *Aster dumosa* identified as code number 98-s-1495, not patented.

*Male, or pollen, parent.*—Proprietary selection of *Aster dumosa* identified as code number 98-r-1494, not patented.

Propagation:

*Type.*—Terminal vegetative cuttings.

*Time to initiate roots.*—Summer: About ten days at 18° C. Winter: About two weeks at 18° C.

*Time to produce a rooted cutting.*—Summer: About 15 days at 18° C. Winter: About 18 days at 18° C.

*Root description.*—Fine; white in color, close to 155D.

*Rooting habit.*—Freely branching.

Plant description:

*Appearance.*—Daisy-type potted *Aster*. Upright with lateral branches outwardly spreading; inverted triangle with uniformly mounded crown. Strong and freely branching growth habit with about 25 lateral branches; dense and full plants. Moderately vigorous.

*Plant height to top of inflorescences.*—About 20 cm.

*Plant height to top of foliar plane.*—About 12 cm.

*Plant width.*—About 24 cm.

*Lateral branches.*—Length: About 6 to 12 cm. Diameter: About 4 mm. Internode length: About 6 mm. Strength: Strong. Texture: Smooth, glabrous. Color: 144B.

*Foliage description.*—Arrangement: Alternate; simple. Length: About 6 cm. Width: About 1.2 cm. Shape: Elliptical to linear. Apex: Acute. Base: Attenuate, clasping. Margin: Entire to slightly serrate. Texture, upper and lower surfaces: Smooth, glabrous. Color: Developing foliage, upper and lower surfaces: 144A. Fully expanded foliage, upper surface: 147A. Fully expanded foliage, lower surface: More gray than 147A. Venation, upper surface: 147A. Venation, lower surface: 148A. Petiole: Length: About 4 cm. Diameter: About 6 mm. Texture, upper and lower surfaces: Smooth, glabrous. Color, upper surface: 145D. Color, lower surface: 144A.

Inflorescence description:

*Appearance.*—Daisy-type inflorescence form with linear-shaped ray florets. Inflorescences terminal and axillary. Disk and ray florets develop acropetally on a capitulum. Inflorescences not fragrant. Inflorescences persistent. Inflorescences face upright to outwardly.

*Flowering response.*—Under natural conditions, plants flower from early August to mid-October in Bonsall, Calif. Uniform flowering habit.

*Inflorescence longevity.*—Inflorescences maintain good color and substance for about seven to ten days on the plant.

*Quantity of inflorescences.*—About 24 open inflorescences per lateral branch.

*Inflorescence bud.*—Height: About 8 mm. Diameter: About 8 mm. Shape: Oblate. Color: 92B.

*Inflorescence diameter.*—About 4.2 cm.

*Inflorescence height.*—About 1.4 cm.

*Diameter of disc.*—About 2 cm.

*Receptacle diameter.*—About 1 cm.

*Ray florets.*—Shape: Linear. Orientation: Initially upright, then nearly horizontal. Aspect: Straight, mostly flat. Length: About 2 cm. Width: About 3 mm. Apex: Slightly emarginate. Base: Acute. Margin: Entire. Texture: Smooth, glabrous, satiny. Number of ray florets per inflorescence: About 46 arranged in two or three whorls. Color: When opening, upper surface: Close to 90B. When opening, lower surface: Close to 85A. Fully opened, upper surface: Close to 90A; color does not fade with development. Fully opened, lower surface: Close to 85A.

*Disc florets.*—Arrangement: Massed at center of receptacle. Shape: Tubular, elongated. Apex: Five-pointed. Length: About 1.1 cm. Diameter, apex: About 3 mm. Diameter, base: Less than 1 mm. Number of disc florets per inflorescence: About 60. Color: Immature: 157A. Mature: Apex: Close to 157A. Mid-section: Close to 157C. Base: Close to 145D.

*Phyllaries.*—Quantities per inflorescence: About 30. Length: About 5 mm. Width: About 1.5 mm. Shape: Lanceolate. Apex: Acute. Base: Truncate, fused. Margin: Entire. Texture, upper and lower surfaces: Smooth. Color, upper and lower surfaces: Close to 147A.

*Peduncles.*—Length: About 5 to 9 cm. Diameter: About 2.5 mm. Angle to vertical: About 45° from vertical. Strength: Strong, flexible. Texture: Smooth, glabrous. Color: 146A.

*Reproductive organs.*—Androecium: Present on disc florets only. Anther shape: Narrowly oblong. Anther size: About 2 by 1 mm. Anther color: Close to 7A. Pollen amount: Scarce. Pollen color: Close to 7A. Gynoecium: Present on ray and disc florets. Pistil length: About 9 mm. Style length: About 7 mm. Style color: Close to 4D. Stigma shape: Bi-parted. Stigma color: Close to 4B. Ovary color: 157C. Pappas: Appearance: Bristle-like, very fine. Length: About 5 mm. Diameter: Less than 1 mm. Color: 157C.

*Seed/fruit.*—Seed and fruit production has not been observed.

Disease/pest resistance: Resistance to pathogens and pests common to *Asters* has not been observed on plants grown under commercial greenhouse conditions.

Garden performance: Plants of the new *Aster* have been observed to tolerate rain, wind and temperatures from −5 to 40° C.

It is claimed:

1. A new and distinct cultivar of *Aster* plant named 'Kiestrbl', as illustrated and described.

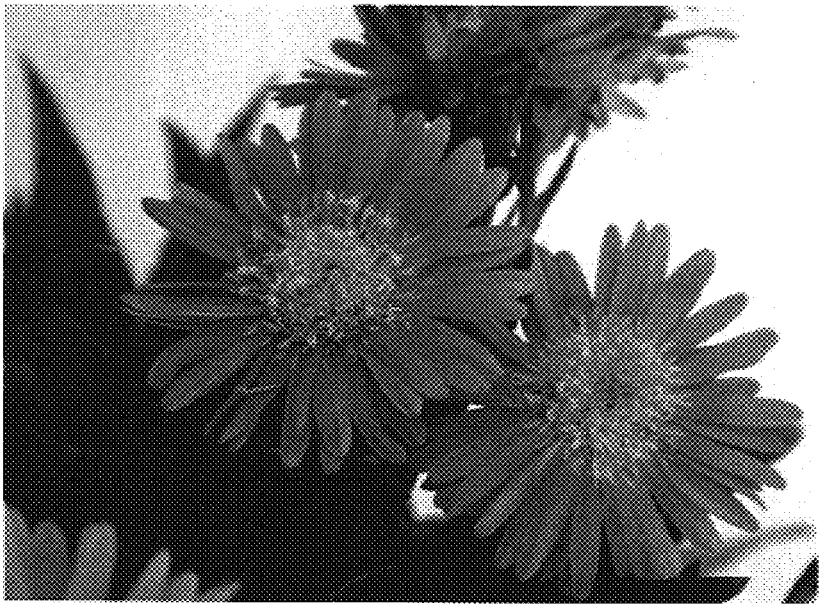
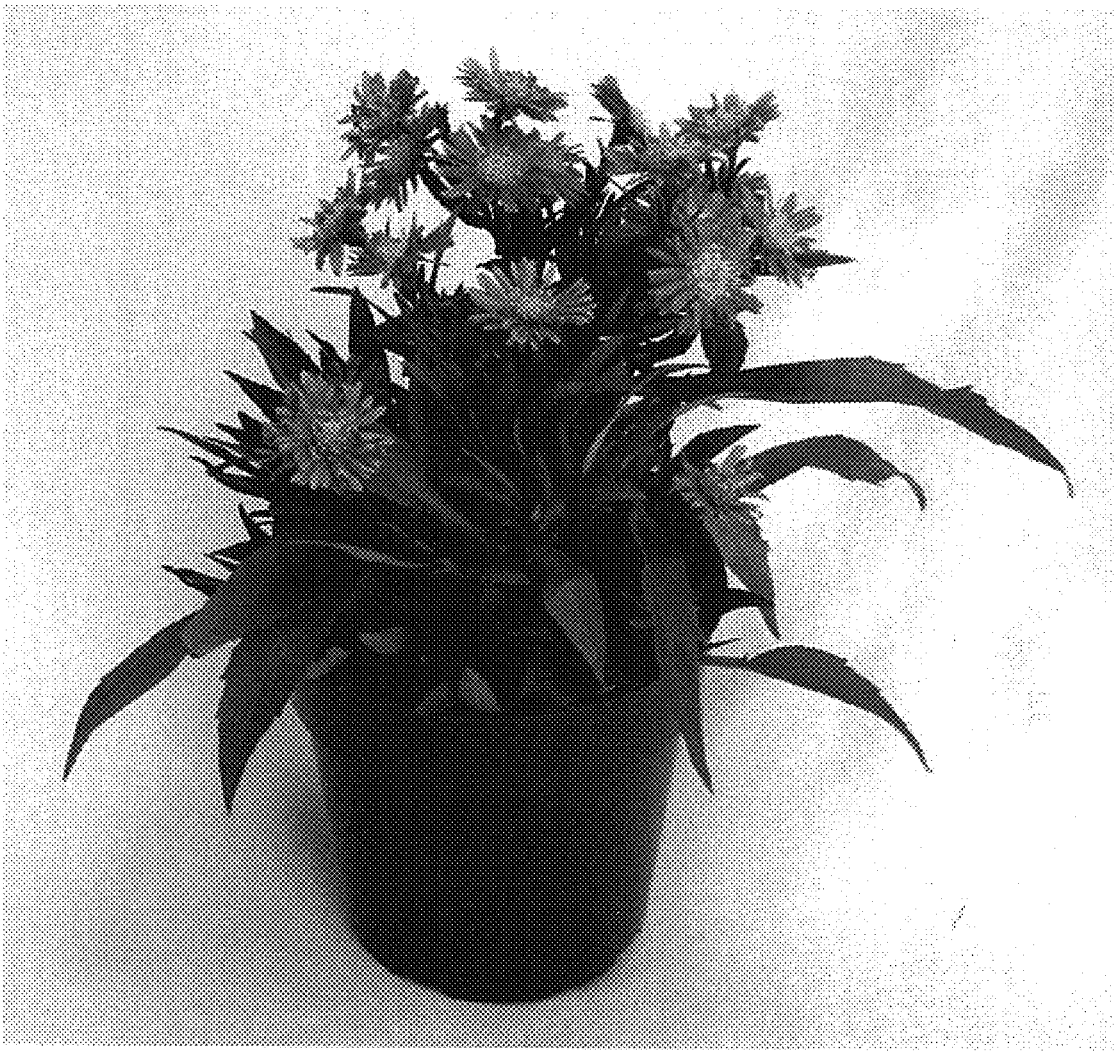

* * * * *